(12) United States Patent
Lamden et al.

(10) Patent No.: US 11,878,069 B2
(45) Date of Patent: Jan. 23, 2024

(54) SHAVE-CLEANSER COMPOSITION

(71) Applicant: Dual-Shave LLC, Beverly Hills, CA (US)

(72) Inventors: Nisan David Lamden, Beverly Hills, CA (US); Neil Badlani, Santa Fe Springs, CA (US)

(73) Assignee: Dual-Shave LLC, Beverly Hills, CA (US)

( * ) Notice: Subject to any disclaimer, the term of this patent is extended or adjusted under 35 U.S.C. 154(b) by 54 days.

(21) Appl. No.: 17/182,919

(22) Filed: Feb. 23, 2021

(65) Prior Publication Data

US 2021/0386638 A1 Dec. 16, 2021

Related U.S. Application Data

(63) Continuation of application No. 15/996,942, filed on Jun. 4, 2018, now abandoned.

(60) Provisional application No. 62/515,966, filed on Jun. 6, 2017.

(51) Int. Cl.
| | |
|---|---|
| *A61K 8/38* | (2006.01) |
| *A61K 8/41* | (2006.01) |
| *A61K 8/46* | (2006.01) |
| *A61K 8/36* | (2006.01) |
| *A61K 8/86* | (2006.01) |
| *A61Q 19/10* | (2006.01) |
| *A61K 8/81* | (2006.01) |
| *A61Q 9/02* | (2006.01) |
| *A61K 8/98* | (2006.01) |
| *A61Q 19/08* | (2006.01) |

(52) U.S. Cl.
CPC ............... *A61K 8/38* (2013.01); *A61K 8/361* (2013.01); *A61K 8/416* (2013.01); *A61K 8/466* (2013.01); *A61K 8/8147* (2013.01); *A61K 8/86* (2013.01); *A61Q 9/02* (2013.01); *A61Q 19/10* (2013.01); *A61K 8/986* (2013.01); *A61K 2800/596* (2013.01); *A61Q 19/08* (2013.01)

(58) Field of Classification Search
CPC .......... A61K 8/38; A61K 8/361; A61K 8/416; A61K 8/466
See application file for complete search history.

(56) References Cited

U.S. PATENT DOCUMENTS

| | | | | |
|---|---|---|---|---|
| 5,204,093 | A * | 4/1993 | Victor | ...................... A61Q 9/02 514/859 |
| 5,614,180 | A | 3/1997 | Chung | |
| 8,933,007 | B1 * | 1/2015 | Perry | ................... A61K 8/9789 510/141 |
| 2010/0226948 | A1 * | 9/2010 | Jitpraphai | ................ A61K 9/06 424/402 |
| 2013/0323228 | A1 | 12/2013 | Norman | |
| 2014/0018508 | A1 | 1/2014 | Masubuchi et al. | |

FOREIGN PATENT DOCUMENTS

CN 102028651 4/2011

OTHER PUBLICATIONS

Sun et al. (CN 102028651, published: Apr. 27, 2011), English machine translation obtained on Sep. 29, 2022. (Year: 2022).*
Final Office Action dated Sep. 25, 2020, from U.S. Appl. No. 15/996,942.
Non-Final Office action dated Mar. 24, 2020, from U.S. Appl. No. 15/996,942.

* cited by examiner

*Primary Examiner* — Genevieve S Alley
(74) *Attorney, Agent, or Firm* — Foley & Lardner LLP

(57) ABSTRACT

Provided are skincare compositions that include a bactericide, one or more surfactants, water, and optionally saturated fatty acid. The composition may include a bactericide, surfactants (e.g., anionic and/or zwitterionic), saturated fatty acid, and no more than about 50 wt % water. Alternatively, the composition may include a bactericide, surfactants (e.g., anionic and/or nonionic), and at least about 50 wt % water. Commonly, the skincare compositions may include benzoyl peroxide and goat milk. The compositions may be used for various applications including cleaning the skin and as a shaving cream.

18 Claims, No Drawings

SHAVE-CLEANSER COMPOSITION

CROSS-REFERENCE TO RELATED APPLICATION

This application is a continuation of U.S. application Ser. No. 15/996,942, filed Jun. 4, 2018, which claims the benefit of and priority to U.S. Provisional Application No. 62/515,966, filed Jun. 6, 2017, the contents of each of which are incorporated herein by reference in its entirety.

BACKGROUND

Most individuals separately buy and use a variety of personal care products (e.g., cleansers, lotions, moisturizers, perfumes/colognes, deodorant, shaving cream, toothpaste, etc.). It would be advantageous to consumers to reduce the number of personal care products needed, while maintaining the desired effects of individual personal care products.

SUMMARY

The present application relates generally to the field of personal care compositions and, in particular, compositions which may be especially useful as a shave cream and/or skin (e.g., facial) cleanser.

The composition may include a bactericide, one or more surfactants, water, and optionally saturated fatty acid. In one embodiment, the composition may include a bactericide, surfactants (e.g., anionic and/or zwitterionic), saturated fatty acid, and no more than about 50 wt % water. In another embodiment, the composition may include a bactericide, surfactants (e.g., anionic and/or nonionic), and at least about 50 wt % water. In some embodiments, the compositions may include about 1 to 10 wt % of a bactericide, about 10 to 30 wt % of an anionic surfactant, about 1 to 20 wt % of a zwitterionic surfactant, about 10 to 30 wt % of a first saturated $C_{10}$-$C_{20}$ fatty acid and about 1 to 20 wt % of a second saturated $C_{10}$-$C_{20}$ fatty acid, and less than about 50 wt % water. In some embodiments, the composition may include about 1 to 10 wt % of a bactericide; about 5 to 30 wt % of an anionic surfactant; more than about 50 wt % water; about 0.5 to 10 wt % of an acrylic based polymer; about 1 to 10 wt % of a pH adjustor; about 0.1 to 5 wt % of a preservative comprising phenoxyethanol, benzoic acid, ethylhexylglycerin, or a combination of two or more thereof; about 0.1 to 5 wt % of a nonionic surfactant comprising a PEG-based nonionic surfactant; about 0.01 to 1 wt % of a chelating agent; less than about 0.1 wt % of animal milk (e.g., goat milk); about 0.5 to 5 wt % of a humectant; and 0 to about 5 wt % of fragrance.

The present technology also provides compositions that may include benzoyl peroxide and an animal milk such as goat milk.

Typically, the bactericide includes a peroxide such as benzoyl peroxide. Commonly, the present compositions may have a pH of about 5-8.

The present compositions may provide one or more of the following: improved skin texture, improved skin glow, treat and/or prevent acne, or a combination thereof. In some embodiments, the present compositions may provide skin anti-aging properties.

DETAILED DESCRIPTION

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

In one aspect, the present technology provides a composition that includes a bactericide, an anionic surfactant, zwitterionic surfactant, a saturated fatty acid comprising a first saturated $C_{10}$-$C_{20}$ fatty acid and a second saturated $C_{10}$-$C_{20}$ fatty acid, and no more than about 50 wt % water, wherein the composition is a skincare composition.

In another aspect, the present technology provides a composition that includes a bactericide, surfactants (e.g., anionic and/or nonionic), and at least about 50 wt % water, wherein the composition is a skincare composition. In some embodiments, the composition may include a bactericide, an anionic surfactant, and at least about 50 wt % water. In some embodiments, the composition may include a bactericide, an anionic surfactant, at least about 50 wt % water, and goat milk.

In some embodiments, the bactericide may be a peroxide, active chlorine compounds (e.g., hypochlorites and chloramines), cationic surfactants (e.g., quaternary ammonium cations, chlorhexidine, glucoprotamine, and octenidine dihydrochloride), or natural extracts (e.g., garlic extract). In some embodiments, the bactericide includes a peroxide. Preferably, the peroxide includes benzoyl peroxide. In some embodiments, the composition may include about 1 wt % to about 10 wt % of the bactericide including about 3 wt % to about 8 wt %, about 3 wt % to about 7 wt %, about 5 wt % to about 7 wt %, or about 4 wt % to about 6 wt %.

The compositions may further include one or more of the following additional components: additional surfactant(s), fatty acid(s), preservative(s), acrylic based polymer(s), pH adjustor(s), chelating agent(s), botanical extract, skin conditioning agent(s) such as urea derivative(s), animal milk, humectant(s), and fragrance(s).

In some embodiments, the composition may include an anionic surfactant. In some embodiment, the composition may include two or more anionic surfactants. In some embodiments, the anionic surfactant may provide cleaning, foaming, and/or washing capability properties to the compositions. The anionic surfactant may include a sulfate, sulfonate, sulfosuccinate, sarcosine, sarcosinate, isethionate, taurate, or a combination of two or more thereof. In some embodiments, the anionic surfactant may be a sodium, potassium, calcium, magnesium, or ammonium salt. In some embodiments, the anionic surfactant may include a sulfonate salt and/or sulfate salt. In some embodiments, the anionic surfactant may include a sulfonate salt. For example, the sulfonate salt may be a $C_{12}$-$C_{18}$ sulfonate salt (e.g., $C_{14}$-$C_{16}$ sulfonate salt). In some embodiments, the sulfonate salt may be unsaturated (e.g., unsaturated $C_{12}$-$C_{18}$ including unsaturated $C_{14}$-$C_{16}$ sulfonate salt). In some embodiments, the sulfonate salt may include an anion with the formula $RCH=CH-SO_3^-$, wherein R may be a $C_{11}$-$C_{13}$ alkyl. In some embodiments, the sulfonate salt may include $RCH=CH-SO_3^-Na^+$, wherein R may be a $C_{11}$-$C_{13}$ alkyl. In the anionic surfactant may include a taurate salt such as an alkyl taurate salt. In some embodiments, the alkyl taurate salt may include a methyl cocyl taurate such as sodium methyl cocyl taurate. In some embodiments, the composition may include $RCH=CH-SO_3^-Na^+$, wherein R may be a $C_{11}$-$C_{13}$ alkyl and sodium methyl cocyl taurate. In some embodiments, the anionic surfactant may include a sulfate salt such as laureth sulfate. In some embodiments, the composition may include about 5 wt % to about 30 wt % of the anionic surfactant including about 10 wt % to about 30 wt %, about 10 wt % to about 20 wt %, or about 14 wt % to about 18 wt %.

In some embodiments, the composition may include a zwitterionic surfactant. In some embodiment, the composition may include two or more zwitterionic surfactants. In some embodiments, the zwitterionic surfactant may be amphoteric. In some embodiments, the zwitterionic surfactant may provide cleaning, skin conditioning, skin nourishing, foaming, and/or foam boosting properties to the compositions. In some embodiments, the zwitterionic surfactant may include a cationic and anionic center in the same molecule separated by one or more atoms. Commonly, the cationic part may include a primary, secondary, or tertiary amine or a quaternary ammonium. In some embodiments, the anionic part may include a sulfonate, sulfate, phosphonate, phosphate, or carboxylate. For example, the zwitterionic surfactant may include a sultaine, betaine, or phospholipid. In some embodiments, the zwitterionic surfactant may include a quaternary ammonium such as a betaine. In some embodiments, the betaine may include an alkylamidopropyl betaine. For example, the composition may include a cocamidopropyl betaine. Another type of zwitterionic surfactant that may be included have a cationic and anionic center on two adjacent atoms. For example, the zwitterionic surfactant may include amine oxide functionality. In some embodiments, the zwitterionic surfactant may include a lauryl amine oxide. In some embodiment, the composition may include cocamidopropyl betaine and lauryl amine oxide. In some embodiment, the composition may include about 1 wt % to about 20 wt % of the anionic surfactant including about 5 wt % to about 15 wt % or about 8 wt % to about 12 wt %.

In some embodiments, the composition may include nonionic surfactants. In some embodiment, the composition may include one or more nonionic surfactants. In some embodiment, the composition may include two or more nonionic surfactants. In some embodiments, the nonionic surfactant may provide cleaning, skin conditioning, skin nourishing, skin soothing, and/or skin softening properties to the compositions. In some embodiments, the nonionic surfactant may include one or more ethoxy groups. In some embodiments, the nonionic surfactant may include a polyethylene glycol (PEG) based surfactant. For example, the composition may include a PEG glycerol fatty acid ester such as glycereth-2 cocoate. In some embodiments, the nonionic surfactant may include a fatty acid diester. For example, the composition may include a $C_{16}$-$C_{20}$ saturated fatty acid diester such as glycol distearate. In some embodiment, the composition may include about 0.1 wt % to about 10 wt % of the nonionic surfactant including about 1 wt % to about 10 wt %, about 1 wt % to about 5 wt %, about 0.1 wt % to about 5 wt %, about 0.1 wt % to about 0.5 wt %, or about 2 wt % to about 4 wt %.

In some embodiments, the composition may include a preservative. The preservative may be a natural or synthetic preservative. In some embodiments, the preservative may include an antioxidant. In some embodiments, the preservative may also provide skin conditioning properties. Exemplary natural preservatives include, but are not limited to, Vitamin E, rosemary oil extract, and grapefruit seed extract. Exemplary synthetic preservatives include, but are not limited to, parabens and paraben based preservatives, phenoxyethanol, benzoic acid, ester derivatives of hydroxybenzoic acid, and ethylhexylglycerin. In some embodiments, the preservative may include phenoxyethanol, benzoic acid, ethylhexylglycerin, or a combination of two or more thereof. In some embodiments, the composition may include about 0.1 wt % to about 5 wt % preservative including about 0.5 wt % to about 5 wt %, about 1 wt % to about 5 wt %, about 2 wt % to about 4 wt %, or about 0.1 wt % to about 0.5 wt %.

In some embodiments, the composition may include one or more nonionic surfactants and one or more preservatives. In some embodiments, the composition may include polyethylene glycol (PEG) based nonionic surfactant including, but not limited to, PEG glycerol fatty acid ester (e.g., glycereth-2 cocoate). In some embodiments, the composition may include phenoxyethanol, benzoic acid, ethylhexylglycerin, or a combination of two or more thereof. In some embodiments, the composition may include glycereth-2 cocoate, phenoxyethanol, benzoic acid, and ethylhexylglycerin. In some embodiments, the composition may include Lincoserve™ PE955. In some embodiments, the composition may include about 0.1 wt % to about 5 wt % of the one or more nonionic surfactants and one or more preservatives together. In some embodiments, the composition may include about 0.1 wt % to about 1 wt %, about 0.2 wt % to about 1 wt %, or about 0.4 wt % to about 0.6 wt % of the one or more nonionic surfactants and one or more preservatives together.

In some embodiments, the composition may include a saturated fatty acid. Preferably, the saturated fatty acid includes two or more saturated fatty acids. In some embodiments, the saturated fatty acid may include a first saturated $C_{10}$-$C_{20}$ fatty acid and a second saturated $C_{10}$-$C_{20}$ fatty acid. In some embodiments, the first saturated $C_{10}$-$C_{20}$ fatty acid may include a saturated $C_{12}$-$C_{16}$ fatty acid such as myristic acid. In some embodiments, the second saturated $C_{10}$-$C_{20}$ fatty acid may include a saturated $C_{16}$-$C_{20}$ fatty acid such as stearic acid. In some embodiments, the composition may include a third saturated $C_{10}$-$C_{20}$ fatty acid. In some embodiments, the third saturated $C_{10}$-$C_{20}$ fatty acid may include a saturated $C_{10}$-$C_{24}$ fatty acid such as lauric acid. In some embodiment, the composition may include about 10 wt % to about 30 wt % of a first saturated $C_{10}$-$C_{20}$ fatty acid including about 10 wt % to about 20 wt % or about 12 wt % to about 16 wt %. In some embodiment, the composition may include about 1 wt % to about 20 wt % of a second saturated $C_{10}$-$C_{20}$ fatty acid including about 5 wt % to about 10 wt % or about 6 wt % to about 8 wt %. In some embodiment, the composition may include about 1 wt % to about 10 wt % of a third saturated $C_{10}$-$C_{20}$ fatty acid including about 1 wt % to about 5 wt % or about 2.5 wt % to about 4.5 wt %.

In some embodiments, the composition may include an acrylic based polymer. Typically, the acrylic based polymer is crosslinked. In some embodiments, the acrylic based polymer may include polymerized monomers of acrylic acid, acrylic acid ester(s), methacrylic acid, methacrylic acid ester(s), polyalkenyl polyethers, or a combination of two or more thereof. In some embodiments, the acrylic based polymer may include Carbopol® (e.g., Carbopol® 910, 934, 940, 941, 934P, and/or Ultrez 10). In some embodiment, the composition may include about 0.5 wt % to about 10 wt % of an acrylic based polymer including about 1 wt % to about 10 wt %, about 3 wt % to about 7 wt %, or about 1 wt % to about 3 wt %.

In some embodiments, the composition may include a pH adjustor such as a base. In some embodiments, the base may include hydroxide (e.g., potassium hydroxide and/or sodium hydroxide). In some embodiment, the composition may include about 0.01 wt % to about 10 wt % of a base including about 1 wt % to about 10 wt %, about 3 wt % to about 7 wt %, about 0.1 wt % to about 3 wt %, about 0.1 wt % to about 2 wt %, about 0.1 wt % to about 1 wt %, or about 0.2 wt % to about 0.5 wt %. Typically, the composition has a pH of about 5 to about 8, more preferably about 5.5 to about 7.5 or about 6 to about 8 (e.g., about 5.5 to about 6, 6 to about 6.5, about 6.5 to about 7, or about 7 to about 7.5).

In some embodiments, the composition may include a chelating agent. In some embodiments, the chelating agent may include an ethylenediaminetetraacetic acid (EDTA) salt. Exemplary chelating agents include, but are not limited to, disodium, calcium disodium, and/or tetrasodium EDTA. In some embodiments, the composition may include disodium EDTA. In some embodiment, the composition may include about 0.01 wt % to about 1 wt % of the chelating agent including about 0.01 wt % to about 0.1 wt % or about 0.04 wt % to about 0.0.06 wt %.

In some embodiments, the composition may include botanical extract. Nonlimiting botanical extracts include green tea, chamomile, cucumber fruit (including cucumber peel), sea buckthorn, *ginseng* root, burdock root, grape seed, olive leaf, banaba leaf, rosehip, willow bark, horse chestnut, sunflower, sacha inchi, maca, chia, algae, aloe vera, *arnica, bacillus* ferment, bamboo, calendula, chaparral, coconut water, desert fruit, edelweiss, goldenseal, kakadu, licorice, lychee, mallow, *marrubium*, mulberry root, oatmeal, *rhodiola*, rhubarb root, rosemary leaf, sage, sea fennel, sea kelp, soapwort, watermelon, white tea, witch hazel, *eucalyptus*, ginger, wintergreen, oat kernel, and combinations of two or more thereof. In some embodiments, the botanical extract includes extracts of *eucalyptus*, ginger, wintergreen, oat kernel, or a combination of two or more thereof. In some embodiment, the composition may include less than about 1 wt % of the botanical extract including less than about 0.1 wt %.

In some embodiments, the composition may include a urea derivative such as allantoin. In some embodiment, the composition may include less than about 0.1 wt % of the urea derivative including less than about 0.05 wt %.

In some embodiments, the composition may include one or more humectants. Humectants include, but are not limited, triethylene glycol, tripropylene glycol, propylene glycol, polypropylene glycol, glycerin, sorbitol, hexylene and butylene glycol, urea, collagen, and combinations of two or more thereof. In some embodiments, the humectant may include glycerin. In some embodiments, the composition may include about 0.5 wt % to about 10 wt % humectant including about 0.5 wt % to about 5 wt %, about 1 wt % to about 5 wt %, or about 0.5 wt % to about 2 wt %.

In some embodiments, the composition may include animal milk. Nonlimiting examples of animal milk includes cow, goat, water buffalo, bison, camel, sheep, yak, reindeer, and elk milk. In some embodiments, the composition may include goat milk. In some embodiment, the composition may include less than about 0.1 wt % of the animal milk including less than about 0.05 wt %, less than about 0.03 wt %, or less than about 0.02 wt %, or less than about 0.01 wt %. In some embodiment, the composition may include about 0.001 wt % to about 0.1 wt % of the animal milk. In some embodiment, the composition may include about 0.005 wt % to about 0.05 wt %, about 0.007 wt % to about 0.03 wt %, or about 0.009 wt % to about 0.02 wt % of the animal milk.

In some embodiments, the compositions may include no more than about 50 wt % water. In some embodiments, the compositions may include less than about 50 wt % water. For example, the compositions may include about 15 wt % to about 30 wt % water or about 15 wt % to about 25 wt %. In another embodiment, the compositions may include at least about 50 wt % water. In some embodiments, the compositions may include at least about 60 wt % water. For example, the compositions may include about 50 wt % to about 80 wt % water or about 60 wt % to about 70 wt %. Preferably, the water is deionized water.

In some embodiments, the composition may include about 1 to 10 wt % of the bactericide; about 10 to 30 wt % of the anionic surfactant; about 1 to 20 wt % of the zwitterionic surfactant; about 10 to 30 wt % of the first saturated $C_{10}$-$C_{20}$ fatty acid and about 1 to 20 wt % of the second saturated $C_{10}$-$C_{20}$ fatty acid; and less than about 50 wt % water. In some embodiments, about 3 to 7 wt % of the bactericide; about 10 to 20 wt % of the anionic surfactant; about 5 to 10 wt % of the zwitterionic surfactant; about 10 to 20 wt % of the first saturated $C_{10}$-$C_{20}$ fatty acid and about 5 to 10 wt % of the second saturated $C_{10}$-$C_{20}$ fatty acid; and about 15 to 30 wt % water.

In some embodiments, the composition may include one or more of the following: about 1 to 10 wt % of the third saturated $C_{10}$-$C_{20}$ fatty acid; about 1 to 10 wt % of the acrylic based polymer; about 1 to 10 wt % of the pH adjustor; about 0.1 to 5 wt % of the preservative; about 1 to 15 wt % of the zwitterionic, nonionic, and/or anionic surfactant; about 0.01 to 1 wt % of the chelating agent; less than about 1 wt % of the botanical extract; less than about 0.1 of the urea derivative; less than about 0.1 of the animal milk; about 1 to 10 wt % of the humectant; and about 0.1 to 5 wt % of the fragrance. In some embodiments, the composition may include one or more of the following: about 1 to 5 wt % of the third saturated $C_{10}$-$C_{20}$ fatty acid; about 3 to 7 wt % of the acrylic based polymer; about 3 to 7 wt % of the pH adjustor; about 1 to 5 wt % of the preservative; about 4 to 8 wt % of the zwitterionic, nonionic, and/or anionic surfactant; about 0.01 to 0.1 wt % of the chelating agent; less than about 0.1 wt % of the botanical extract; less than about 0.05 of the urea derivative; less than about 0.05 of the animal milk; about 1 to 5 wt % of the humectant; and about 0.1 to 1 wt % of the fragrance.

In some embodiments, the composition may include about 1 to 10 wt % of a bactericide, about 5 to 30 wt % of an anionic surfactant, and at least about 50 wt % water. In some embodiments, the composition may include a bactericide, an anionic surfactant, and at least about 50 wt % water. In some embodiments, the composition may include about 1 to 10 wt % of a bactericide, about 5 to 30 wt % of an anionic surfactant, at least about 50 wt % water, and less than about 0.1 wt % animal milk (e.g., goat milk). In some embodiments, the composition may include about 1 to 10 wt % of a bactericide comprising a peroxide; about 5 to 30 wt % of an anionic surfactant comprising $C_{12}$-$C_{18}$ sulfonate salt; more than about 50 wt % water; about 0.5 to 10 wt % of an acrylic based polymer; about 1 to 10 wt % of a pH adjustor comprising a base; about 0.1 to 5 wt % of a preservative comprising phenoxyethanol, benzoic acid, ethylhexylglycerin, or a combination of two or more thereof, about 0.1 to 5 wt % of a nonionic surfactant comprising a PEG-based nonionic surfactant; about 0.01 to 1 wt % of a chelating agent; less than about 0.1 wt % of animal milk (e.g., goat milk); about 0.5 to 5 wt % of a humectant; and 0 to about 5 wt % of fragrance.

In one aspect, the present technology provides a composition that includes about 1 to 10 wt % of a bactericide comprising a peroxide; about 10 to 30 wt % of an anionic surfactant comprising $C_{12}$-$C_{18}$ sulfonate salt; about 1 to 20 wt % of a zwitterionic surfactant comprising a quaternary ammonium; about 10 to 30 wt % of a $C_{12}$-$C_{16}$ saturated fatty acid and about 1 to 20 wt % of a $C_{16}$-$C_{20}$ saturated fatty acid; less than about 50 wt % water; about 1 to 10 wt % of a saturated $C_{10}$-$C_{14}$ fatty acid; about 1 to 10 wt % of an acrylic based polymer; about 1 to 10 wt % of a pH adjustor comprising a base; about 0.1 to 5 wt % of a preservative comprising phenoxyethanol, benzoic acid, ethylhexylglycerin, or a combination of two or more thereof, about 1 to 15 wt % of a zwitterionic, nonionic, and/or anionic surfactant comprising an amine oxide, PEG-based nonionic surfactant, fatty acid diester, and/or alkyl taurate salt; about 0.01 to 1 wt % of a chelating agent; less than about 1 wt % of a botanical extract; less than about 0.1 of a urea derivative; less than about 0.1 of animal milk; about 1 to 10 wt % of a humectant; and about 0.1 to 5 wt % of fragrance. In some embodiments, the composition is a skincare composition.

In one aspect, the present technology provides a composition that includes about 3 to 7 wt % of benzoyl peroxide; about 10 to 20 wt % of $RCH{=}CH{-}SO_3^-Na^+$, wherein R is $C_{11}$-$C_{13}$ alkyl; about 5 to 10 wt % of cocamidopropyl betaine; about 10 to 20 wt % of myristic acid and about 5 to 10 wt % of stearic acid; about 15 to 30 wt % water; about 1 to 5 wt % of lauric acid; about 3 to 7 wt % of an acrylic based polymer comprising polymerized monomers of acrylic acid, acrylic acid ester(s), methacrylic acid, and/or methacrylic acid ester(s); about 3 to 7 wt % of potassium hydroxide and/or sodium hydroxide; about 1 to 5 wt % of phenoxyethanol, benzoic acid, and ethylhexylglycerin; about 4 to 8 wt % of lauryl amine oxide, glycereth-2 cocoate, glycol distearate, and sodium methyl cocoyl taurate; about 0.01 to 0.1 wt % of an EDTA salt; less than about 0.1 wt % of a botanical extract comprising extracts of *eucalyptus*, ginger, wintergreen, oat kernel, or a combination of two or more thereof; less than about 0.05 of allantoin; less than about 0.05 of goat milk; about 1 to 5 wt % of glycerin; and about 0.1 to 1 wt % of fragrance. In some embodiments, the composition is a skincare composition.

In one aspect, the present technology provides a composition that includes about 1 to 10 wt % of a bactericide comprising a peroxide; about 5 to 30 wt % of an anionic surfactant comprising $C_{12}$-$C_{18}$ sulfonate salt; at least about 50 wt % water; about 0.5 to 10 wt % of an acrylic based polymer; about 1 to 10 wt % of a pH adjustor comprising a base; about 0.1 to 5 wt % of a preservative comprising phenoxyethanol, benzoic acid, ethylhexylglycerin, or a combination of two or more thereof, about 0.1 to 5 wt % of a nonionic surfactant comprising a PEG-based nonionic surfactant; about 0.01 to 1 wt % of a chelating agent; less than about 0.1 wt % of animal milk; about 0.5 to 5 wt % of a humectant; and 0 to about 5 wt % of fragrance. In some embodiments, the composition is a skincare composition.

In one aspect, the present technology provides a composition that includes about 3 to 7 wt % benzoyl peroxide; about 10 to 20 wt % of an anionic surfactant comprising $RCH{=}CH{-}SO_3^-Na^+$, wherein R is $C_{11}$-$C_{13}$ alkyl; at least about 60 wt % water; about 1 to 3 wt % of an acrylic based polymer; about 0.1 to 1 wt % of a potassium hydroxide and/or sodium hydroxide; about 0.1 to 1 wt % of glycereth-2 cocoate, phenoxyethanol, benzoic acid, and ethylhexylglycerin; about 0.01 to 0.1 wt % of an EDTA salt; about 0.001 wt % to about 0.1 wt % goat milk; about 0.5 to 2 wt % of glycerin; and 0 to about 2 wt % of fragrance. In some embodiments, the composition is a skincare composition.

The present technology also provides a composition that includes benzoyl peroxide and an animal milk such as goat milk. In some embodiments, the composition may include about 1 wt % to about 10 wt % of the benzoyl peroxide including about 3 wt % to about 7 wt % or about 4 wt % to about 6 wt %. In some embodiment, the composition may include less than about 0.1 wt % of goat milk including less than about 0.05 wt % or less than about 0.01 wt %. The composition may additionally include any other component described herein.

The compositions described herein may further include other components commonly added to skin care compositions such as, but not limited to, detergent(s), moisturizer(s), dye(s), alcohol amine(s), salicyclic acid, sodium sulfacetamide, thickening agent, emollients (e.g., petrolatum, lanolin, mineral oil, and ceramides), and exfoliants (e.g., alpha-hydroxy acids).

In some embodiments, the compositions described herein may have a viscosity of about 80,000 cps to 180,000 cps. For example, the compositions may have a viscosity of about 90,000 cps to 130,000 cps or 100,000 cps to 120,000 cps. In some embodiments, the compositions described herein may a specific gravity of about 0.90 to 1.10. For example, the compositions may have a viscosity of about 0.99 to 1.02.

The present technology also provides methods of using the compositions. In some embodiments, the composition may be used as a shaving cream and/or skin (e.g., facial) cleanser. The composition may be applied to the skin and used following known methods of using shaving creams and/or skin cleansers. For example, the composition may be applied by the user's hand(s) or a device to the skin followed by shaving and/or massaging the composition into the skin. In some embodiments, the skin may then be rinsed with water.

The present technology also provides methods for making the compositions. Typically, the process includes mixing together most or all components at room temperature (e.g., 20-25° C.) and pressure (e.g., about 1 atm). In some embodiments, the process may include heating the mixture except the bactericide, preservative, botanical extract, and/or animal milk. In some embodiments, the mixture may be heated from about 45° C. to about 80° C. (e.g., about 55° C. to about 70° C.).

In some embodiments, the water, chelating agent, and humectant are mixed together to form mixture A1. In some embodiments, the acrylic based polymer is added to mixture A1 to form mixture A2. In some embodiments, the zwitterionic and anionic surfactants are mixed together to form mixture B. Mixture B may then be added to mixture A2 to form mixture I. In some embodiments, the saturated fatty acid and nonionic surfactant are mixed together to form mixture C. Mixture C may then be added to mixture I to form mixture II. To mixture II a premixed aqueous solution of the pH adjustor may be added to form mixture III. Once mixture III is cooled to at least about 40° C., the bactericide, preservative, botanical extract, and/or animal milk may be added. Last, if needed, additional pH adjustor may be added to arrive at a desired pH.

In some embodiments, under continual mixing the water, chelating agent, acrylic based polymer, and humectant may be added together followed by homogenizing of the mixture. With the mixing continued, the pH adjustor may be added followed by the anionic surfactant, bactericide, preservative, nonionic surfactant, and/or animal milk. Last, if needed, additional pH adjustor may be added to arrive at a desired pH.

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

As used herein, "composition" refers to any liquid, foam, solid, gel, and/or paste substance having more than one component.

As used herein, "fragrance" refers to any perfume, odor-eliminator, odor masking agent, the like, and combinations thereof. In some embodiments, a fragrance is any substance which may have an effect on a consumer, or user's, olfactory senses.

As used herein, "skincare composition" refers to any composition that may be applied topically to the skin. Preferably, the skincare composition is a cosmetically acceptable skincare composition (e.g., compatible with the skin and aids transport of active molecule onto and through the skin). Preferably, the skincare composition spreads easily and well when applied to the skin. In some embodiments, the skincare composition may be a shaving cream and/or skin (e.g., facial) cleanser. In some embodiments, the skincare composition may be a shaving cream and a skin cleanser.

As used herein, "wt. %" refers to the weight percentage of an ingredient in the total formula. For example, an off-the-shelf commercial composition of Formula X may only contain 70% active ingredient X. Thus, 10 g of the off-the-shelf composition only contains 7 g of X. If 10 g of the off-the-shelf composition is added to 90 g of other ingredients, the wt. % of X in the final formula is thus only 7%.

As used herein, "surfactant" refers to any agent that lowers the surface tension of a liquid, for example water. Exemplary surfactants which may be suitable for use with the present invention are described herein. In one embodiment, surfactants may be selected from the group consisting of anionic, non-ionic, amphoteric, zwitterionic, and combinations thereof.

EXAMPLES

The examples herein are provided to illustrate advantages of the present technology and to further assist a person of ordinary skill in the art with preparing or using the compositions of the present technology. The examples herein are also presented in order to more fully illustrate the preferred aspects of the present technology. The examples should in no way be construed as limiting the scope of the present technology, as defined by the appended claims. The examples can include or incorporate any of the variations or aspects of the present technology described above. The variations or aspects described above may also further each include or incorporate the variations of any or all other variations or aspects of the present technology.

Example 1: An exemplary formulation of the present compositions was prepared and is presented in Table 1 below.

TABLE 1

Composition A

| COMPONENT | FORMULA (Wt. %) |
|---|---|
| Benzoyl peroxide | 5 |
| Water | 21 |
| Sodium $C_{14}$-$C_{16}$ Olefin Sulfonate | 15 |
| Myristic acid | 14 |
| Cocamidopropyl betaine | 8 |
| Stearic acid | 7.2 |
| Carbopol ® Aqua SF - Polymer | 5 |
| Potassium hydroxide | 4.61 |
| Lauric acid | 3.6 |
| Glycerin | 3 |
| Glycol distearate | 2.4 |
| Lauryl amine oxide | 1.5 |
| Sodium methyl cocoyl taurate | 1.5 |
| Phenoxyethanol | 0.8 |
| Benzoic acid | 0.8 |
| ethylhexylglycerin | 0.8 |
| Glycereth-2 cocoate | 0.8 |
| fragrance | 0.3 |
| Disodium EDTA | 0.05 |
| Eucalyptus Globulus Leaf Extract | 0.01 |
| Zingiber Officinale (ginger) root extract | 0.01 |
| Gaultheria Procumbens (wintergreen) Leaf Extract | 0.01 |
| Avena Sativa (Oat) Kernal Extract | 0.01 |
| Allantoin | 0.01 |
| Goat Milk | 0.001 |

Composition A was prepared by mixing the water and disodium EDTA at room temperature in a first beaker. Once the disodium EDTA completely dissolved, the glycerin was added and mixed for about 10 minutes. Next, Carbopol® Aqua SF—Polymer was added and mixed for another 10 minutes. A 50% solution of potassium hydroxide was then added and mixed for 10 minutes to provide mixture I.

In a second beaker, a 40% solution of sodium $C_{14}$-$C_{16}$ olefin sulfonate and cocamidopropyl betaine were added together and mixed for about 10 minutes. Sodium methyl cocoyl taurate was then added and mixed for another 10 minutes followed by the addition of lauryl amine oxide. Mixing of the solution continued while heating to about 60-65° C. The solution of the second beaker was then added to the first beaker.

In a third beaker, a stearic acid, lauric acid, myristic acid, and glycol distearate were mixed together and heated to about 60-65° C. until dissolved. The solution of the third beaker was then added to the previously mixed first and second beaker solution. To this mixture, a 50% aqueous solution of potassium hydroxide was added. The resulting mixture was continually stirred for about another 20 minutes while cooling to about 35-40° C. Last, the benzoyl peroxide, phenoxyethanol, benzoic acid, ethylhexylglycerin, fragrance, *Eucalyptus globulus* leaf extract, ginger root extract, wintergreen leaf extract, oat kernel extract, allantoin, and goat milk were added sequentially under continued mixing. The pH of the composition was determined and adjusted if needed with additional 50% aqueous solution of potassium hydroxide.

The properties of the composition was analyzed and are provided in Table 2.

TABLE 2

Test Methods and Properties of Composition A

| Test Method | Specification | Result |
| --- | --- | --- |
| Appearance (TMHS0001) | Opaque, Thick Gel | Pass |
| Color (TMHS0002) | White to Off-White | Pass |
| Odor (TMHS0003) | Characteristic, TMS | Pass |
| pH (TMHS0004) | 7.0-8.0 | 7.2 |
| Viscosity (TMHS0006) | 80,000-180,000 cps (Tentative) | 110,000 cps |
| Specific Gravity (TMHS0005) | 0.990-1.020 | 1.009 |

Example 2: An exemplary formulation of the present compositions was prepared and is presented in Table 3 below.

TABLE 3

Composition B

| COMPONENT | FORMULA (Wt. %) |
| --- | --- |
| Benzoyl peroxide | 5.7 |
| Water | 67.5 |
| Sodium $C_{14}$-$C_{16}$ Olefin Sulfonate | 15 |
| Carbopol ® Ultrez 10 | 1.8 |
| Potassium hydroxide | 0.39 |
| Glycerin | 1 |
| Lincoserve ™ PE955 (Phenoxyethanol, benzoic acid, ethylhexylglycerin, glycereth-2 cocoate) | 0.5 |
| Disodium EDTA | 0.05 |
| Goat Milk | 0.01 |

Composition B was prepared by slowly adding disodium EDTA and Carbopol® Ultrez 10 to water at room temperature in a tank under continued propeller mixing (speed 50-75%) and sweep mixing (speed 50-75%). Once completely dissolved, the glycerin was added under continued mixing. Mixing was continued for 10-15 minutes. Next, the in-tank homogenizer (speed 25-50%) was started and recirculation using a suitable diaphragm pump and mixing was continued for about 20-30 minutes or until the mixture was clump free. The homogenizer was stopped and a 50% solution of potassium hydroxide was slowly added under continued mixing. Mixing and recirculation was continued for about 20-30 minutes. The sodium $C_{14}$-$C_{16}$ olefin sulfonate was added under continued mixing. Mixing was continued for 20-30 minutes. The benzoyl peroxide, Lincoserve™ PE955, and goat milk were then added under continued mixing. Mixing was continued for another 20-30 minutes.

The properties of the composition was analyzed and are provided in Table 4.

TABLE 4

Test Methods and Properties of Composition B

| Test Method | Specification | Result |
| --- | --- | --- |
| Appearance (TMHS0001) | Opaque, Thick Gel | Pass |
| Color (TMHS0002) | White to Off-White | Pass |
| Odor (TMHS0003) | Characteristic, TMS | Pass |
| pH (TMHS0004) | 7.0-8.0 | 7.2 |
| Viscosity (TMHS0006) | 80,000-180,000 cps (Tentative) | 110,000 cps |
| Specific Gravity (TMHS0005) | 0.990-1.020 | 1.009 |

EQUIVALENTS

While certain embodiments have been illustrated and described, a person with ordinary skill in the art, after reading the foregoing specification, can effect changes, substitutions of equivalents and other types of alterations to the compositions of the present technology as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, or compositions, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A method of shaving face skin, the method comprising:
   (a) applying to the face skin a composition comprising:
      i) about 5 to 7 wt % of the benzoyl peroxide;
      ii) 15 to 30 wt % of $C_{12}$-$C_{18}$ sulfonate salt as the only anionic surfactant;
      iii) at least about 50 wt % water;
      iv) about 0.5 to 10 wt % of an acrylic based polymer;
      v) a pH adjustor comprising a base;
      vi) about 0.1 to 5 wt % of a preservative comprising phenoxyethanol, benzoic acid, ethylhexylglycerin, or a combination of two or more thereof;
      vii) 0 to about 5 wt % of a nonionic surfactant comprising a PEG-based nonionic surfactant or a fatty acid diester;
      viii) about 0.01 to 1 wt % of a chelating agent
      ix) 0.001 wt % to 0.05 wt % goat milk;
      x) about 0.5 to 5 wt % of a humectant; and
      xi) 0 to about 5 wt % of fragrance;
      wherein the composition is in a form selected from a liquid, a foam, a gel, and a paste
   (b) massaging the composition into the face skin;
   (c) shaving the face skin; and
   (d) rinsing the face skin with water.

2. The method of claim 1, wherein the $C_{12}$-$C_{18}$ sulfonate salt comprises RCH=CH—$CH_2$-$SO_3^-Na^+$, wherein R is $C_{11}$-$C_{13}$ alkyl.

3. The method of claim 1, wherein the composition comprises at least about 60 wt % water.

4. The method of claim 1, wherein the composition has a pH of about 5 to about 8.

5. The method of claim 1, wherein the acylic based polymer is about 3 wt % to about 7 wt %.

6. The method of claim 1, wherein the nonionic surfactant is glycereth-2 cocoate.

7. The method of claim 1, wherein the nonionic surfactant is a $C_{16}$-$C_{20}$ saturated fatty acid diester.

8. The method of claim 1, wherein the nonionic surfactant is about 1 wt % to about 5 wt %.

9. The method of claim 1, wherein the chelating agent is an ethylenediaminetetraacetic acid (EDTA) salt.

10. The method of claim 1, wherein the $C_{12}$-$C_{18}$ sulfonate salt comprises RCH=CH—$CH_2$—$SO_3^-Na^+$, wherein R is $CH_{11}$-$C_{13}$ alkyl.

11. The method of claim 1, wherein the composition comprises at least about 60 wt % water.

12. The method of claim 1, wherein the composition has a pH of about 5 to about 8.

13. The method of claim 1, wherein the acylic based polymer is about 3 wt % to about 7 wt %.

14. The method of claim 1, wherein the nonionic surfactant is glycereth-2 cocoate.

15. The method of claim 1, wherein the nonionic surfactant is a $C_{16}$-$C_{20}$ saturated fatty acid diester.

16. The method of claim 1, wherein the nonionic surfactant is about 1 wt % to about 5 wt %.

17. The method of claim 1, wherein the chelating agent is an ethylenediaminetetraacetic acid (EDTA) salt.

18. A method of shaving face skin, the method comprising:
    (a) applying to the face skin a composition consisting of:
       i) about 5 to 7 wt % of the benzoyl peroxide;
       ii) 15 to 30 wt % of $C_{12}$-$C_{18}$ sulfonate salt;
       iii) at least about 50 wt % water;
       iv) about 0.5 to 10 wt % of an acrylic based polymer;
       v) a pH adjustor comprising a base;
       vi) about 0.1 to 5 wt % of a preservative comprising phenoxyethanol, benzoic acid, ethylhexylglycerin, or a combination of two or more thereof;
       vii) 0 to about 5 wt % of a nonionic surfactant comprising a PEG-based nonionic surfactant or a fatty acid diester;
       viii) about 0.01 to 1 wt % of a chelating agent;
       ix) 0.001 wt % to 0.05 wt % goat milk;
       x) about 0.5 to 5 wt % of a humectant; and
       xi) 0 to about 5 wt % of fragrance;
       wherein the composition is in a form selected from a liquid, a foam, a gel, and a paste
    (b) massaging the composition into the face skin;
    (c) shaving the face skin; and
    (d) rinsing the face skin with water.

* * * * *